(12) United States Patent
Paul, Jr.

(10) Patent No.: US 8,500,772 B2
(45) Date of Patent: Aug. 6, 2013

(54) DISTAL PROTECTION DEVICE

(75) Inventor: Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 405 days.

(21) Appl. No.: 11/688,430

(22) Filed: Mar. 20, 2007

(65) Prior Publication Data

US 2007/0219579 A1    Sep. 20, 2007

Related U.S. Application Data

(60) Provisional application No. 60/783,945, filed on Mar. 20, 2006.

(51) Int. Cl.
*A61M 29/00* (2006.01)

(52) U.S. Cl.
USPC ............ 606/200; 606/159; 606/191; 606/194

(58) Field of Classification Search
USPC ....................................................... 606/200
See application file for complete search history.

(56) References Cited

U.S. PATENT DOCUMENTS

| | | | |
|---|---|---|---|
| 5,814,064 A | 9/1998 | Daniel et al. | |
| 5,827,324 A | 10/1998 | Cassell et al. | |
| 5,989,280 A * | 11/1999 | Euteneuer et al. | 623/1.1 |
| 6,001,118 A | 12/1999 | Daniel et al. | |
| 6,053,932 A | 4/2000 | Daniel et al. | |
| 6,152,946 A | 11/2000 | Broome et al. | |
| 6,245,089 B1 | 6/2001 | Daniel et al. | |
| 6,258,115 B1 | 7/2001 | Dubrul | |
| 6,346,116 B1 | 2/2002 | Brooks et al. | |
| 6,371,969 B1 | 4/2002 | Tsugita et al. | |
| 6,616,680 B1 | 9/2003 | Thielen | |
| 6,616,682 B2 | 9/2003 | Joergensen et al. | |
| 6,663,652 B2 | 12/2003 | Daniel et al. | |
| 6,716,231 B1 | 4/2004 | Rafiee et al. | |
| 6,726,703 B2 | 4/2004 | Broome et al. | |
| 6,740,061 B1 | 5/2004 | Oslund et al. | |
| 6,773,448 B2 | 8/2004 | Kusleika et al. | |
| 6,793,666 B2 | 9/2004 | Hansen et al. | |
| 6,872,216 B2 | 3/2005 | Daniel et al. | |
| 2003/0083608 A1 | 5/2003 | Evans et al. | |
| 2003/0083692 A1 | 5/2003 | Vrba et al. | |
| 2003/0109824 A1 | 6/2003 | Anderson et al. | |
| 2003/0130682 A1 | 7/2003 | Broome et al. | |

(Continued)

FOREIGN PATENT DOCUMENTS

| | | |
|---|---|---|
| WO | WO 03037218 A1 | 5/2003 |
| WO | WO 2004096089 A2 | 11/2004 |

*Primary Examiner* — Gary Jackson
*Assistant Examiner* — Kevin Everage
(74) *Attorney, Agent, or Firm* — Woodard, Emhardt, Moriarty, McNett & Henry LLP

(57) ABSTRACT

The present invention provides, in certain aspects, devices and methods for protecting the body from downstream embolization. In one embodiment, a distal protection device comprises a shaft and a jacket with the shaft being received within the jacket. The device also includes a filter, which is supported by a wire cone that has one end attached to the jacket and an opposite end attached to the shaft. The shaft is rotatable relative to the jacket to reduce the size of the cone for capturing embolic debris within the wire cone. The invention also provides such devices in combination with instruments (e.g., balloon stent catheters) for treating stenosis and other similar conditions.

20 Claims, 3 Drawing Sheets

U.S. PATENT DOCUMENTS

| | | |
|---|---|---|
| 2003/0135162 A1 | 7/2003 | Deyette et al. |
| 2003/0187475 A1* | 10/2003 | Tsugita et al. ............... 606/200 |
| 2003/0191493 A1 | 10/2003 | Epstein et al. |
| 2003/0225418 A1 | 12/2003 | Esksuri et al. |
| 2004/0116831 A1 | 6/2004 | Vrba |
| 2004/0236368 A1 | 11/2004 | McGuckin et al. |
| 2005/0004597 A1 | 1/2005 | McGuckin et al. |
| 2005/0055048 A1* | 3/2005 | Dieck et al. ................. 606/200 |
| 2005/0085842 A1 | 4/2005 | Eversull et al. |
| 2005/0090858 A1* | 4/2005 | Pavlovic ...................... 606/200 |
| 2005/0096691 A1 | 5/2005 | Groothuis et al. |
| 2005/0124876 A1 | 6/2005 | Douk et al. |
| 2005/0131510 A1 | 6/2005 | Chen et al. |
| 2006/0287668 A1* | 12/2006 | Fawzi et al. ................. 606/200 |

\* cited by examiner

DISTAL PROTECTION DEVICE

BACKGROUND OF THE INVENTION

The present invention relates to an emboli capturing method and device.

Various procedures are used to treat stenosis in the vascular system including balloon angioplasty, and ablation procedures such as thrombectomy, and atherectomy. Stenotic debris can be created by such treatments which can move with the blood flow in the vascular system causing significant problems. Such debris may also occur when treating stenotic vein grafts (CABG), renal stenting and carotid artery interventions. Improved methods and devices are needed for preventing emboli from causing damage to the vascular system and similar areas where there is risk of downstream embolism.

SUMMARY OF INVENTION

One embodiment of the invention might involve a distal protection device comprising a shaft and a jacket with the shaft being received within the jacket. A filter is supported by a wire cone which has one end attached to the jacket and an opposite end attached to the shaft. The shaft is rotatable relative to the jacket to reduce the size of the cone for capturing embolic debris within the wire cone.

Another embodiment of the invention includes a method of capturing and disposing of emboli by providing a distal protection device including a jacket and a shaft received within the jacket. A coiled cone of wire has one end attached to the jacket and an opposite end attached to the shaft. Mesh is mounted on the cone. The device is inserted in a body lumen downstream of a stenosed region of the lumen. The coiled cone is expanded by rotating the shaft relative to the jacket. The stenosed region is treated to correct the stenosis resulting in emboli moving downstream into the mesh on the cone. The coiled cone is reduced by rotating the shaft relative to the jacket and the distal protection device is withdrawn from the body lumen.

Further objects, embodiments, forms, benefits, aspects, features and advantages of the present invention may be obtained from the description, drawings, and claims provided herein.

DESCRIPTION OF THE PREFERRED EMBODIMENT

Figure 1:
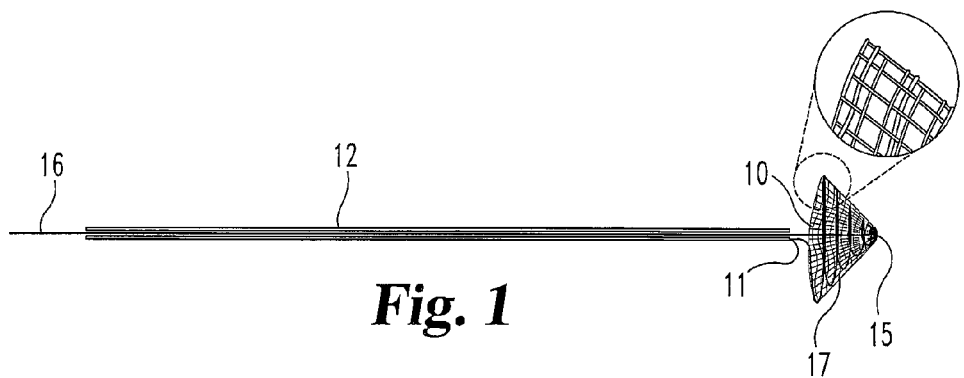
FIG. 1 is a side elevation partially in section of the distal protection device in open position.

For the purposes of promoting understanding of the principles of the invention, reference will now be made to the embodiment illustrated in the drawings and specific language will be used to describe the same. It will nevertheless be understood that no limitation of the scope of the invention is hereby intended and alterations and modifications in the illustrated device, and further applications of the principles of the present invention as illustrated herein being contemplated as would normally occur to one skilled in the art to which the invention relates.

Figure 2:
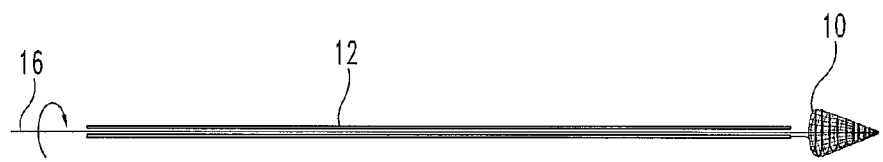
FIG. 2 is a side elevation similar to FIG. 1 showing the device partially closed.
Figure 3:
FIG. 3 is a elevation partially in section showing the device in closed position.
Figure 4:
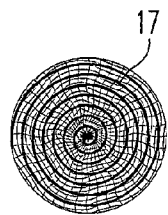
FIG. 4 is an end elevation showing the device in the same position as FIG. 1.

FIG. 1 shows the device 9 in open position. The device is designed to be inserted in the vascular system or in other similar areas where there is risk of downstream embolization. The device includes a coiled cone 10 formed of wire which is connected at one end 11 to an outer jacket 12 and it is connected at the other end 15 to a shaft 16. The wire of the coiled cone 10 is woven through a mesh 17 so that the coil can move freely to allow expansion and contraction of the coiled cone. FIG. 2 shows the device partially closed and FIG. 3 shows the device entirely closed. The closure is accomplished by rotating the shaft 16 relative to the jacket 12. The mesh 17 is porous, preferably having pores in the range of 80 to 110 microns and the coiled cone wire is smaller in cross sectional size (to the 80 to 110 microns) in order to allow weaving through the pores of the mesh. The shaft 16 is preferably formed of an alloy of nickel and titanium known as Nitinol and the wire of the cone 10 is formed preferably of a shape memory polymer or metal.

The device of FIGS. 1-4 may be inserted into the vascular system or other body lumen independently of the instrument selected to perform treatment of the stenosis or, alternatively the outer jacket 12 may function as a wire guide for the instrument used to perform the treatment of the stenosis. In either event, the treatment of the stenosis occurs upstream of the coiled cone 10 and accompanying mesh 17 so that the mesh functions to allow the blood or fluid to pass through the coiled cone but also functions to trap the stenotic particles in the coiled cone upstream of the mesh. The distal protection device of FIGS. 1-4 is positioned in the open position of FIG. 1 when it is being used to perform the filtering.

After the treatment of the stenosis has been completed and the risk of further emboli creation is no longer present, the coiled cone 10 is reduced in size to the configuration of FIG. 2 and further to the configuration of FIG. 1. The reduction in size is accomplished by rotating the shaft 16 relative to the jacket 12. The rotation may be accomplished manually or by means of a motor. The emboli captured within the cone and mesh are then removed from the body lumen by withdrawing the distal protection device from the body lumen.

Figure 5:
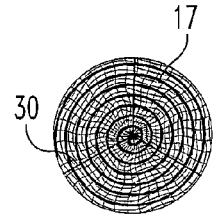
FIG. 5 is an end elevation showing another distal protection device of the invention.

Additionally, an inventive device can incorporate one or more adaptations to enhance movement of the coiled cone. Illustratively and referring now to FIG. 5, one or more rails 30 or other similar elongate members can extend along successive coils of the cone (e.g., in a generally longitudinal fashion, and perpendicular relative to the coils as shown). Adaptations of this sort can be formed with a variety of materials (e.g., metals, synthetic polymeric materials, etc.), and may be rigid, semi-flexible, or flexible. Also, such adaptations need not be fixed to the coil wire. In some instances, a rail is retained in association with the coiled cone, yet the two are able to translate along one another as the cone changes shape. Those skilled in the art will recognize other suitable means for facilitating desirable expansion and contraction of the coiled cone, and therefore, they are encompassed by the present invention.

Figure 6:
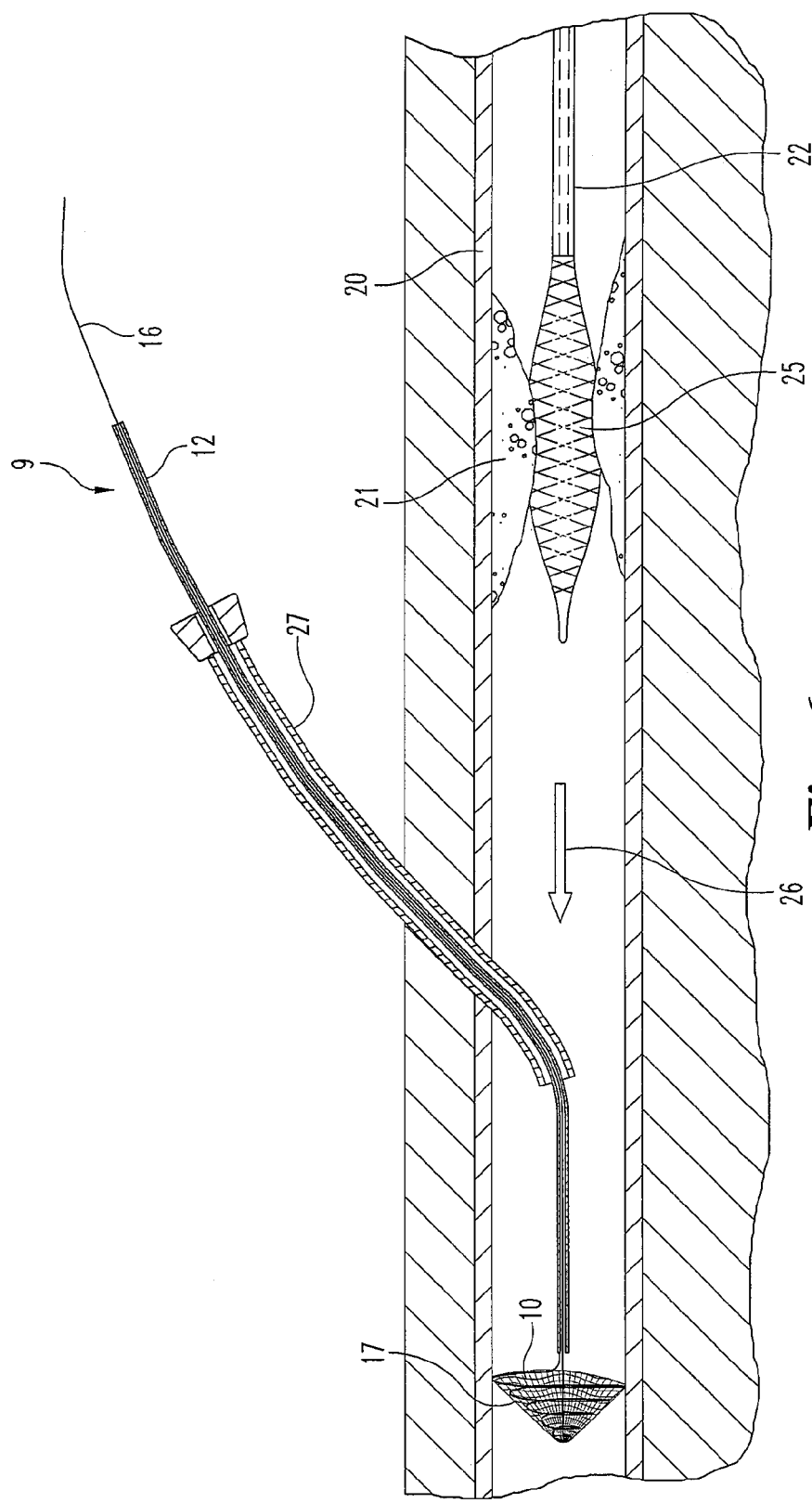
FIG. 6 is a schematic vessel showing one example of the use of the distal protection device.

FIG. 6 shows one method of use in the distal protection device. In FIG. 6, the body lumen 20 is shown as having plaque or stenosis 21 which is restricting the flow of blood. This stenosis may be treated by means of a balloon stent catheter 22 which is inserted into the stenosis and expanded to open up the size of the passageway in a manner well known to those skilled in the art. The catheter includes a stent 25 which is plastically deformed holding the lumen open and facilitating blood flow. The balloon catheter is then removed from the lumen. This procedure can produce emboli which moves downstream in the direction of the arrow 26.

Prior to the introduction of the balloon stent and the expanding of the stent to open up the body lumen, the distal protection device is inserted into the body lumen 20 downstream of the stenosis 21. The insertion is accomplished by means of an introducer sheath 27. When the distal protection device 9 is inserted through the introducer sheath, it is in the closed position of FIG. 3, but without emboli received within the mesh 17. After insertion, it is opened to the position of FIG. 1 and FIG. 6 in contact with the wall of the lumen 20 wherein device 9 filters the blood flow moving downstream from the stenting procedure. After the catheter 22 has been removed and the risk of further emboli moving downstream from the stenting procedure is over, the distal protection device is manipulated by rotating the shaft 16 relative to the jacket 12 so that the emboli are captured in the mesh 17 of the coiled cone 10 and the coiled cone is reduced in size to the configuration of FIG. 3. The distal protection device is then removed from the body lumen by withdrawal through the introducer sheath 27.

The mesh is porous preferably in the range of 80 to 110 microns. The structure of the mesh 17 may be made from numerous base materials, such as polymers including bioabsorbable or biostable polymers; nonmetallic biocompatible materials including polyamides, polyolefins (e.g., polypropylene or polyethylene), nonabsorbable polyesters (e.g., polyethylene terephthalate) or bioabsorbable aliphatic polyesters (e.g. homopolymers or copolymers of lactic acid, glycolic acid, lactide, glycolide, paradioxanone, trimethylene carbonate or .episolon.-caprolactone); polymeric materials (e.g., poly-L-lactic acid, polycarbonate, polyethylene terephthalate or engineering plastics such as thermotropic liquid crystal polymers (LCPs)); biocompatible polymeric materials (e.g., cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene or polytetrafluoroethylene); degradable or biodegradable polymers, plastics, natural (e.g., animal, plant or microbial) or recombinant material (e.g., polylactic acid, polyglycolic acid, polyanhydride, polycarprolactone, polyhydroxybutyrate valerate, polydepsipeptides, nylon copolymides, conventional poly (amino acid) synthetic polymers, pseudo-poly(amino acids) or aliphatic polyesters (e.g., polyglycolic acid (PGA), polylactic acid (PLA), polyalkylene succinates, polyhydroxybutyrate (PHB), polybutylene diglycolate, poly epsilon-caprolactone (PCL), polydihydropyrans, polyphosphazenes, polyorthoesters, polycyanoacrylates, polyanhydrides, polyketals, polyacetals, poly(.alpha.-hydroxy-esters), poly (carbonates), poly(imino-carbonates), poly(.beta.-hydroxyesters) or polypeptides)); polyethylene terephthalate (e.g., dacron or mylar); expanded fluoropolymers (e.g., polytetrafluoroethylene (PTFE)); fluorinated ethylene propylene (FEP); copolymers of tetrafluoroethylene (TFE) and per fluoro(propyl vinyl ether) (PFA)); homopolymers of polychlorotrifluoroethylene (PCTFE) and copolymers with TFE; ethylene-chorotrifluoroethylene (ECTFE); copolymers of ethylene-tetrafluoroethylene (ETFE); polyvinylidene fluoride (PVDF); polyvinyfluoride (PVF); polyaramids (e.g., kevlar); polyfluorocarbons including polytetrafluoroethylene with and without copolymerized hexafluoropropylene (e.g., Teflon or goretex); expanded fluorocarbon polymers; polyglycolides; polylactides; polyglycerol sebacate; polyethylene oxide; polybutylene terepthalate; polydioxanones; proteoglycans; glycosaminoglycans; poly(alkylene oxalates); polyalkanotes; polyamides; polyaspartimic acid; polyglutarunic acid polymer; poly-p-diaxanone (e.g., PDS); polyphosphazene; polyurethane including porous or nonporous polyurethanes; poly(glycolide-trimethylene carbonate); terpolymer (copolymers of glycolide, lactide or dimethyltrimethylene carbonate); polyhydroxyalkanoates (PHA); polyhydroxybutyrate (PHB) or poly(hydroxybutyrate-co-valerate) (PHB-co-HV); poly(epsilon-caprolactone ((e.g., lactide or glycolide); poly(episilon-caprolactone-dimethyltrimethylene carbonate); polyglycolic acid (PGA); poly-L and poly-D (lactic acid) (e.g., calcium phosphate glass); lactic acid/ethylene glycol copolymers; polyarylates (L-tyrosine-derived) or free acid polyarylates; polycarbonates (tyrosine or L-tyosine-derived); poly(esteramides); poly(propylene fumarate-co-ethylene glycol) copolymer (e.g., fumarate anhydrides); polyanhydride esters; polyanhydrides; polyorthoesters; prolastin or silk-elastin polymers (SELP); calcium phosphate (bioglass); compositions of PLA, PCL, PGA ester; polyphosphazenes; polyamino acids; polysaccharides; polyhydroxyalkanoate polymers; various plastic materials; teflon; nylon; block polymers or copolymers; Leica RM2165; Leica RM2155; organic fabrics; biologic agents (e.g., protein, extracellular matrix component, collagen, fibrin); small intestinal submucosa (SIS) (e.g., vacuum formed SIS); collagen or collagen matrices with growth modulators; aliginate; cellulose and ester; dextran; elastin; fibrin; gelatin; hyaluronic acid; hydroxyapatite; polypeptides; proteins; ceramics (e.g., silicon nitride, silicon carbide, zirconia or alumina); bioactive silica-based materials; carbon or carbon fiber; cotton; silk; spider silk; chitin; chitosan (NOCC or NOOC-G); urethanes; glass; silica; sapphire; composites; any mixture, blend, alloy, copolymer or combination of any of these; or various other materials not limited by these examples.

Illustratively, a mesh useful in the invention such as mesh 17 may be formed with a metallic material. Suitable metallic materials include but are not limited to stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). These and other suitable materials (e.g., synthetic polymers such as polyester, polypropylene, nylon and polytetrafluoroethylene) can be provided in filament form and employed as either monofilaments or multi-strand filaments. A filament or strand can have circular, square, rectangular, or irregular cross-sectional shapes. Additionally, a suitable mesh may be constructed in a variety of manners including some that involve braiding, knitting and weaving material. These meshes can have any suitable porosity for a given use, for example, for allowing perfusing blood flow while capturing emboli. These and other suitable materials for providing filtration will be recognized by the skilled artisan, therefore, are encompassed by the present invention.

In some embodiments, a distal protection device works directly with an instrument that is configured to provide upstream treatment of a stenosed region, and in this regard, the invention provides, in certain aspects, apparatuses that include a distal protection device in combination with such an instrument. Those skilled in the art will recognize the large variety of instruments available for treating stenosis and other similar conditions, and will be able to combine these instruments with the distal protection devices described herein without undue experimentation.

In certain forms, a treatment instrument (e.g., a balloon catheter) incorporates a distal protection device directly as a component that extends distally from other parts of the instrument (or can be extended distally in the body lumen from the area of treatment). Although not necessary to broader aspects of the invention, in some instances, the proximal end 11 of the coiled cone wire can be connected to a distal portion of the treatment instrument, thus potentially obviating the need for the outer jacket 12. In other embodiments, a distal protection device is not necessarily attached to the treatment instrument but is extendable through the instrument (e.g., through an instrument lumen) to enable the coiled cone 10 and accompanying mesh 17 to be placed downstream of the stenosed region. Cooperation between the distal protection device and the treatment instrument will, in certain embodiments, be in a controlled fashion; e.g. wherein portions of the distal protection device and treatment instrument engage and potentially translate along one another in a fashion that is predictably controlled by engaged surface features of the two objects.

Figure 7:
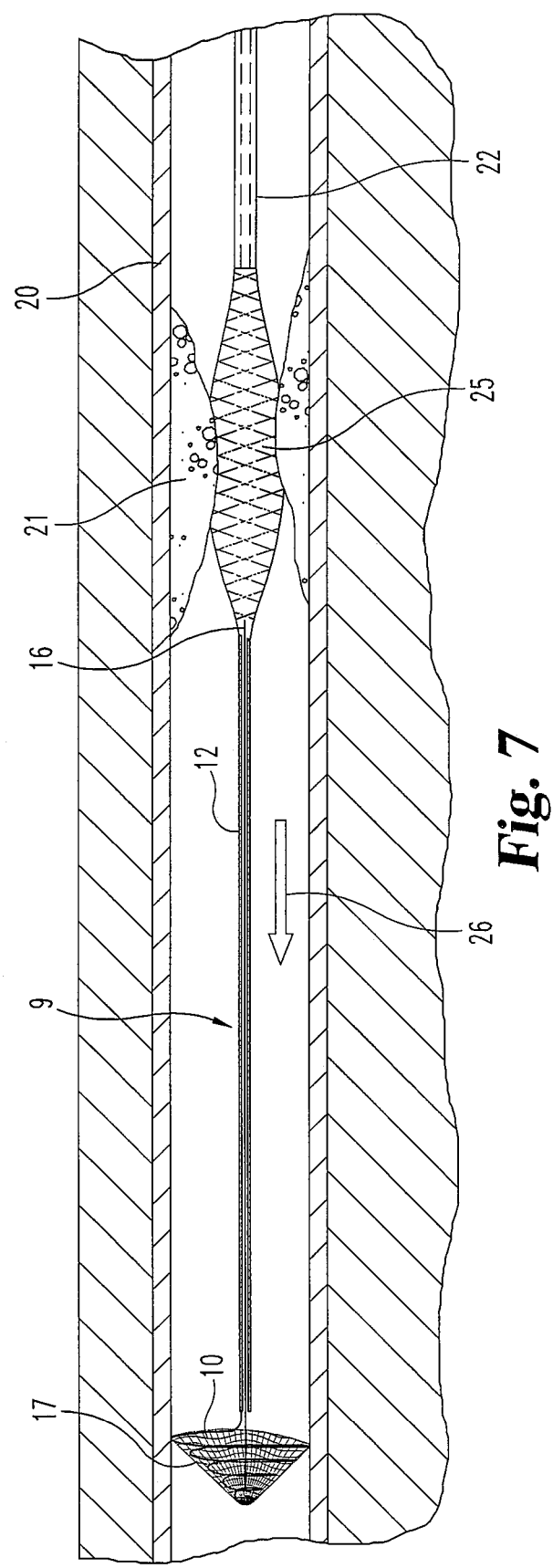
FIG. 7 is a schematic vessel showing another example of the use of the distal protection device.

With reference now to FIG. 7, shown is another method of use in the distal protection device, which is similar to that of FIG. 6 except that the distal protection device 9 extends through the balloon stent catheter 22. Prior to expanding the stent to open up the body lumen, the distal protection device is positioned in the body lumen 20 downstream of the stenosis 21. It is then opened to the position of FIG. 1 in contact with the wall of the lumen 20 wherein device 9 filters the blood flow moving downstream from the stenosed region. The balloon catheter 22 is then operated to expand the stent. Once the risk of further emboli moving downstream from the stenting procedure is over, the distal protection device is manipulated by rotating the shaft 16 relative to the jacket 12 so that the emboli are captured in the mesh 17 of the coiled cone 10 and the coiled cone is reduced in size to the configuration of FIG. 3. The distal protection device is then removed from the body lumen along with or after removal of the balloon catheter 22.

While the invention has been illustrated and described in detail in the drawings and foregoing description, the same is to be considered as illustrative and not restrictive in character, it being understood that only the preferred embodiment have been shown and described and that all changes and modifications that come within the spirit of the invention are desired to be protected. The articles "a", "an", "said" and "the" are not limited to a singular element, and include one or more such elements.

What is claimed is:

1. A distal protection device for capturing embolic debris, comprising:
    a shaft;
    a jacket, said shaft being rotatably received within said jacket;
    a coiled cone formed of wire having a proximal cone end, a distal cone end, and a cone interior extending between said proximal cone end and distal cone end, wherein said proximal cone end is attached to said jacket, said shaft includes a shaft portion extending coaxially within said cone through said cone interior from said proximal cone end to said distal cone end, wherein a distal end of said shaft portion is attached to said distal cone end, and wherein the wire that forms the coiled cone extends in a number of revolutions around said shaft; and
    a mesh filtration element constructed separately from said coiled cone and mounted on said cone, with portions of said wire woven through and movable through openings in the mesh filtration element,
    said shaft being rotatable in a first direction relative to said jacket to increase the number of revolutions of said wire around said shaft and collapse said cone to provide the mesh filtration element in a closed position for capturing embolic debris within said cone,
    said shaft also being rotatable in a second direction opposite said first direction to decrease the number of revolutions of said wire around said shaft and expand said cone to a condition wherein it tapers from a larger diameter at said proximal cone end to a smaller diameter at said distal cone end to provide the mesh filtration element in an open position,
    with said wire portions movable through said openings in the mesh filtration element as the shaft is rotated in said first direction and said second direction to collapse and expand said cone, respectively.

2. The distal protection device of claim 1, wherein said mesh filtration element is comprised of a metallic material.

3. The distal protection device of claim 2, wherein said metallic material is Nitinol.

4. The distal protection device of claim 1, wherein said mesh filtration element is comprised of a synthetic polymeric material.

5. The distal protection device of claim 1, wherein said cone is comprised of a metallic material.

6. The distal protection device of claim 5, wherein said metallic material is Nitinol.

7. The distal protection device of claim 1, wherein said cone has an initial helical shape.

8. The distal protection device of claim 1 wherein the shaft terminates at said distal cone end.

9. A method of capturing and disposing of emboli, comprising:
    inserting a distal protection device according to claim 1 into a body lumen downstream of a stenosed region of the lumen;
    rotating the shaft in said second direction in the body lumen so as to provide said cone in the expanded position;
    treating the stenosed region;
    rotating the shaft in said first direction in the body lumen so as to provide said cone in the collapsed position; and
    withdrawing the distal protection device from the body lumen.

10. The method of claim 9, wherein the inserting is accomplished through an introducer sheath inserted into the body lumen downstream of the stenosed region.

11. An apparatus, comprising:
    a distal protection device according to claim 1; and
    an endoluminally advancable instrument configured to provide treatment to a stenosed region of a bodily lumen upstream of the distal protection device.

12. The apparatus of claim 11, wherein the endoluminally advancable instrument is configured to deliver a stent to the stenosed region.

13. The apparatus of claim 12, wherein the stent is self expandable.

14. The apparatus of claim 12, wherein the stent is balloon expandable.

15. The apparatus of claim 11, wherein the distal protection device is connected to the endoluminally advancable instrument.

16. The apparatus of claim 15, wherein the distal protection device is extendable distally from the endoluminally advancable instrument.

17. The apparatus of claim 11, wherein the endoluminally advancable instrument includes a central lumen, and wherein the distal protection device is extendable through the lumen.

18. A distal protection device for capturing embolic debris, comprising:
- a shaft;
- a jacket, said shaft being rotatably received within said jacket;
- a coiled cone formed of wire having a proximal cone end, a distal cone end, and a cone interior extending between said proximal cone end and distal cone end, wherein said proximal cone end is attached to said jacket, said shaft includes a shaft portion extending coaxially within said cone through said cone interior from said proximal cone end to said distal cone end, wherein a distal end of said shaft portion is attached to said distal cone end, and wherein the wire that forms the coiled cone extends in a number of revolutions around said shaft;
- a mesh filtration element constructed separately from said coiled cone and mounted on said cone with said wire movable with respect to the mesh filtration element as the shaft is rotated relative to the jacket; and
- a plurality of elongate rails extending longitudinally along the coiled cone, wherein said rails are retained in association with the wire of the coiled cone but said rails and said wire are translatable with respect to one another;
- said shaft being rotatable in a first direction relative to said jacket to increase the number of revolutions of said wire around said shaft and collapse said cone to provide the mesh filtration element in a closed position for capturing embolic debris within said cone,
- said shaft also being rotatable in a second direction opposite said first direction to decrease the number of revolutions of said wire around said shaft and expand said cone to a condition wherein it tapers from a larger diameter at said proximal cone end to a smaller diameter at said distal cone end to provide the mesh filtration element in an open position.

19. The device of claim 1, also comprising a plurality of elongate rails extending longitudinally along the coiled cone, wherein said rails are retained in association with the wire of the coiled cone but said rails and said wire are translatable with respect to one another.

20. The device of claim 1, wherein said distal cone end forms a distal most end of the device.

* * * * *